US010287935B2

(12) United States Patent
Verdegan et al.

(10) Patent No.: US 10,287,935 B2
(45) Date of Patent: *May 14, 2019

(54) VIRTUAL FILTER CONDITION SENSOR

(71) Applicant: Cummins Filtration IP, Inc., Columbus, IN (US)

(72) Inventors: Barry Mark Verdegan, Stoughton, WI (US); Peter K. Herman, Stoughton, WI (US); Casey D. Robinson, Columbus, IN (US); Andry Lesmana, Columbus, IN (US); Corey J. Noone, Madison, WI (US)

(73) Assignee: Cummins Filtration IP, Inc., Columbus, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/965,255

(22) Filed: Apr. 27, 2018

(65) Prior Publication Data

US 2018/0245491 A1 Aug. 30, 2018

Related U.S. Application Data

(63) Continuation of application No. 14/762,670, filed as application No. PCT/US2014/012030 on Jan. 17, 2014, now Pat. No. 9,976,456.

(Continued)

(51) Int. Cl.
*G01B 3/44* (2006.01)
*G01B 3/52* (2006.01)
(Continued)

(52) U.S. Cl.
CPC ........... *F01M 11/10* (2013.01); *B01D 35/143* (2013.01); *G01N 15/08* (2013.01); *G01N 2015/084* (2013.01)

(58) Field of Classification Search
CPC ...... F01M 11/10; B01D 35/14; B01D 35/143; G01N 15/08; G01N 2015/084
See application file for complete search history.

(56) References Cited

U.S. PATENT DOCUMENTS 3,568,625 A 3/1971 Cilento
3,611,337 A 10/1971 Balzer et al.
(Continued)

FOREIGN PATENT DOCUMENTS

EP 1 873 369 1/2008

OTHER PUBLICATIONS

International Search Report and Written Opinion issued for PCT/US2014/012030, dated May 8, 2014, 2, 12 pages.

*Primary Examiner* — Toan K Le
(74) *Attorney, Agent, or Firm* — Foley & Lardner LLP

(57) ABSTRACT

A system and method for determining a condition of a filter filtering fuel associated with an engine. Input information relating to the operation of the engine is provided by a plurality of sensors. At least some of the input information is used to determine a plurality of input variables, the plurality of input variables representing a plurality of engine operating conditions including engine run time, engine torque and engine speed. An algorithm incorporating the input variables is used to determine the condition of the filter. Information concerning the condition of the filter may be output to a user such as an operator or service provider.

20 Claims, 4 Drawing Sheets

Related U.S. Application Data

(60) Provisional application No. 61/756,172, filed on Jan. 24, 2013.

(51) Int. Cl.
    *F01M 11/10*     (2006.01)
    *B01D 35/143*     (2006.01)
    *G01N 15/08*     (2006.01)

(56) References Cited

U.S. PATENT DOCUMENTS

| | | | | |
|---|---|---|---|---|
| 3,644,915 | A | 2/1972 | McBurnett | |
| 3,786,920 | A | 1/1974 | Raymond | |
| 3,794,168 | A | 2/1974 | Perkins | |
| 3,812,816 | A | 5/1974 | Juhasz | |
| 3,915,866 | A | 10/1975 | Brown et al. | |
| 3,941,958 | A | 3/1976 | Flesburg | |
| 4,006,083 | A | 2/1977 | Westervelt et al. | |
| 4,189,724 | A | 2/1980 | Onuma et al. | |
| 4,246,110 | A | 1/1981 | Jarrett | |
| 4,343,697 | A | 8/1982 | Miller et al. | |
| 4,500,874 | A | 2/1985 | Jacobi et al. | |
| 4,533,900 | A | 8/1985 | Muhlberger et al. | |
| 4,574,728 | A | 3/1986 | Barnard, Jr. | |
| 4,685,066 | A | 8/1987 | Hafele et al. | |
| 4,729,339 | A | 3/1988 | Whiting | |
| 4,740,140 | A | 4/1988 | Benson | |
| 4,918,426 | A | 4/1990 | Butts et al. | |
| 5,057,821 | A | 10/1991 | Card | |
| 5,089,144 | A | 2/1992 | Ozkahyaoglu et al. | |
| 5,462,679 | A * | 10/1995 | Verdegan | B01D 27/00 210/798 |
| 5,501,791 | A | 3/1996 | Theisen et al. | |
| 5,702,592 | A | 12/1997 | Suri et al. | |
| 5,779,900 | A * | 7/1998 | Holm | B01D 29/15 210/411 |
| 5,858,224 | A | 1/1999 | Schwandt et al. | |
| 5,968,371 | A | 10/1999 | Verdegan et al. | |
| 6,051,144 | A | 4/2000 | Clack et al. | |
| 6,484,127 | B1 | 11/2002 | Langervik | |
| 6,587,767 | B2 | 7/2003 | Letang et al. | |
| 6,741,938 | B2 | 5/2004 | Berndorfer | |
| 6,842,117 | B2 | 1/2005 | Keown | |
| 6,979,361 | B2 | 12/2005 | Mihayiov et al. | |
| 6,989,104 | B2 | 1/2006 | Reamsnyder et al. | |
| 7,225,680 | B2 | 6/2007 | Gustafson et al. | |
| 7,254,518 | B2 | 8/2007 | Eryurek et al. | |
| RE39,845 | E | 9/2007 | Hasfjord et al. | |
| 7,308,829 | B1 | 12/2007 | Beard et al. | |
| 7,373,809 | B2 | 5/2008 | Shattuck et al. | |
| 7,535,347 | B2 | 5/2009 | Larson et al. | |
| 7,581,434 | B1 | 9/2009 | Discenzo et al. | |
| 7,706,938 | B2 | 4/2010 | Palladino | |
| 7,922,914 | B1 | 4/2011 | Verdegan et al. | |
| 9,976,456 | B2 * | 5/2018 | Verdegan | B01D 35/143 |
| 2003/0226809 | A1 | 12/2003 | Zagone et al. | |
| 2007/0023333 | A1 | 2/2007 | Mouhebaty et al. | |
| 2007/0056688 | A1 | 3/2007 | Williams et al. | |
| 2008/0053879 | A1 | 3/2008 | Harris | |
| 2009/0071392 | A1 | 3/2009 | Berry et al. | |
| 2009/0283068 | A1 | 11/2009 | Willison | |
| 2010/0084347 | A1 | 4/2010 | Wilder et al. | |
| 2010/0192679 | A1 | 8/2010 | Brown et al. | |
| 2010/0225492 | A1 | 9/2010 | Abdoulin et al. | |
| 2010/0273068 | A1 | 10/2010 | Crumm et al. | |
| 2011/0054811 | A1 | 3/2011 | Contini et al. | |
| 2011/0209682 | A1 | 9/2011 | Storch et al. | |
| 2011/0307160 | A1 | 12/2011 | Verdegan et al. | |
| 2012/0010786 | A1 | 1/2012 | Stickel et al. | |
| 2012/0046920 | A1 | 2/2012 | Blossfeld et al. | |

* cited by examiner

VIRTUAL FILTER CONDITION SENSOR

CROSS REFERENCE TO RELATED APPLICATIONS

The present application is a continuation of U.S. patent application Ser. No. 14/762,670, filed Jul. 22, 2015, which is a National Stage of PCT Application No. PCT/US2014/012030, filed Jan. 17, 2014, which claims priority to United States Provisional Patent Application Ser. No. 61/756,172, filed Jan. 24, 2013. The contents of these applications are incorporated herein by reference in their entirety and for all purposes.

TECHNICAL FIELD

The present disclosure relates generally to fluid filters used in conjunction with various types of engine systems. More particularly, the present disclosure relates to systems and methods for monitoring the condition of such fluid filters.

BACKGROUND

U.S. Pat. No. 7,922,914, which is incorporated herein by reference in entirety, discloses methods and systems for measuring pressure drop through a filter in the flow path and then using the measured pressure drop, possibly at a normalized state and in conjunction with time and/or other data from the system, to estimate characteristics of the fluid, the filter, and/or a working component supplied with the filtered fluid. Such characteristics could include an operating condition of the filter, the remaining useful life of the filter, the relative contaminant concentration in the fluid, and/or the remaining useful life of a working component supplied with the filtered fluid.

U.S. Patent Application Publication No. US 2011/0307160 A1, which is incorporated herein by reference in entirety, discloses systems, methods, and algorithms for monitoring and indicating filter life. The disclosed systems, methods, and algorithms may be utilized for monitoring and indicating the useful life of a filter in an internal combustion engine.

Filters have a finite service interval, the length of which is governed by the nature and amount of contaminant present in the fluid and conditions of use. Service (or filter change) intervals are normally specified in terms of the distance driven or the length of time before the filter should be replaced or serviced. The common practice of using distance or time to define service intervals is an approximation. In some cases, service intervals may be made based on pressure drop across the filter, but this is not normally done due to cost of adding an additional sensor(s).

Depending on the application, a filter may reach terminal pressure drop earlier or later than the specified service interval. Filters sometimes plug before the specified service interval, particularly when the engine is used in severe duty or dirty environments. This was found through research and experimentation, and is because filter service intervals are established based on expected conditions, not on the conditions that the filter actually experiences.

SUMMARY

This Summary is provided to introduce a selection of concepts that are further described below in the Detailed Description. This Summary is not intended to identify key or essential features of the invention, nor is it intended to be used as an aid in limiting the scope of the invention.

The present inventors have realized that it is desirable to utilize on-board existing sensors in an engine system, notably fuel and lube oil sensors, as condition sensors that determine the condition of the filter and adapt to changes in conditions. The present inventors have realized that it is desirable to provide this functionality without requiring that additional sensors be added to the system, thus reducing cost and complexity. The condition of a filter can refer to the remaining useful life of the filter and/or the status of the filter, i.e., whether the filter has significant remaining useful life, should be serviced, or has reached or exceeded its useful life.

The present inventors have also realized that since premature filter plugging can cause deterioration of engine performance, accelerated wear, and/or increased service costs, it is desirable to have a more accurate means of determining when to replace a filter or to at least to ensure that the filter is not used beyond its useful life. To do this, the effects of duty cycle, application, and filter- and engine-specific factors should be considered. Advance notification of when a filter is approaching the end of its useful life enables the engine operator and/or service personnel to coordinate service activities and production needs, thus reducing costs and increase productivity. As mentioned herein above, it is further desirable that this be accomplished without adding additional sensors to the conventional system.

The present disclosure provides a virtual sensor that determines the condition of a fuel or lube filter using engine run time, torque and speed data. An engine speed sensor and other appropriate engine sensors functionally provide input to a control circuit, such as an engine control module (ECM). The ECM uses the data to determine engine torque. Torque, speed and time data are then used by an algorithm to determine the condition of the filter, and the ECM provides an output to a display or control device to notify the operator, service personnel, or to initiate appropriate response. The disclosure provides for optional adjustable parameters in the algorithm whose values depend on the operating environment, engine, and filter characteristics which can be manually or automatically changed to improve the accuracy of the calculation.

These and other features, together with the organization and manner of operation thereof, will become apparent from the following detailed description when taken in conjunction with the accompanying drawings.

DETAILED DESCRIPTION

In the present description, certain terms have been used for brevity, clearness and understanding. No unnecessary limitations are to be inferred therefrom beyond the requirement of the prior art because such terms are used for descriptive purposes only and are intended to be broadly construed. The different devices, methods and systems described herein may be used alone or in combination with other devices, methods and systems. Various equivalents, alternatives, and modifications are possible.

Figure 1:
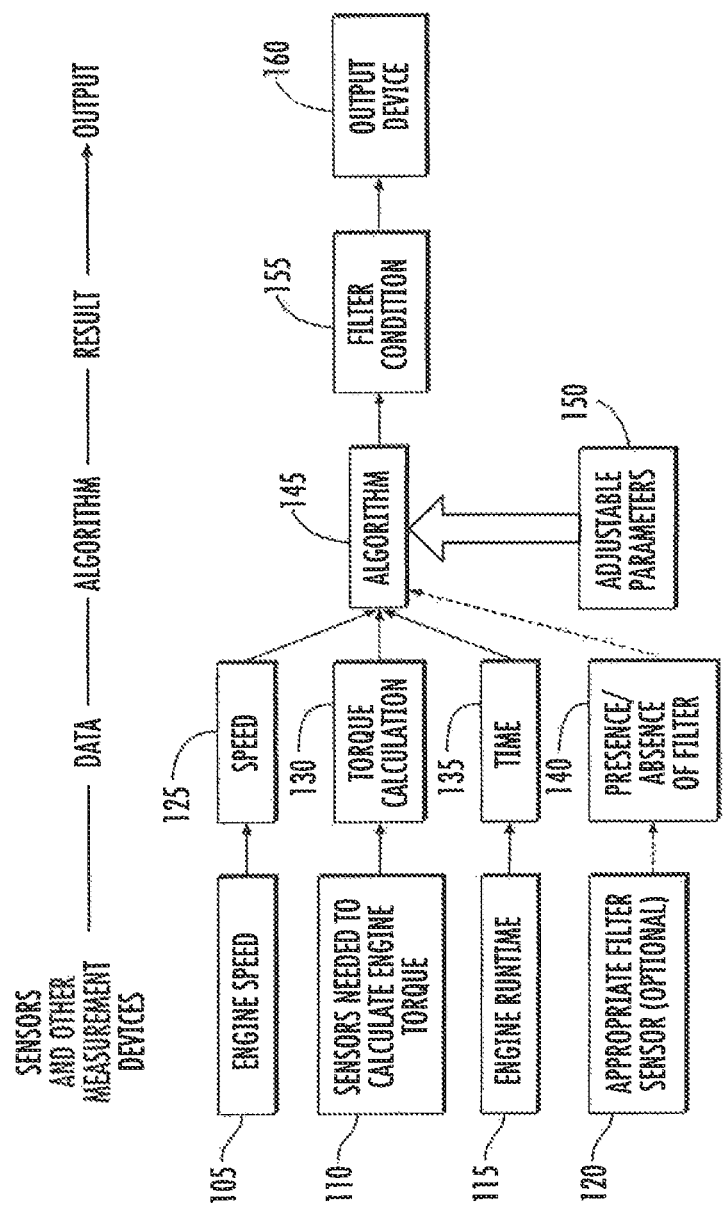
FIG. 1 is a schematic representation of a virtual filter condition sensor in accordance with various exemplary embodiments.

The virtual filter condition sensor, schematically illustrated in FIG. 1, estimates the condition of engine fuel and/or lube oil filters. It obtains, among other possible things, engine run time, engine torque, and engine speed data. Engine speed can be measured directly using on-board sensors. In modern diesel engines, engine torque is typically continually calculated by the ECM from measured inputs, such as the engine speed, air intake manifold pressure, and throttle position. The sensors required to do the calculation are typically already present on-board the engine. Time, torque and speed data is functionally transmitted or otherwise made available as inputs to the ECM or other controller. It should be understood that when an ECM is referenced herein, the associated structure, functionality and features may be equally applicable to other types of controllers or control units.

In FIG. 1, a number of functions are typically resident in the ECM. Data from other sensors, e.g., temperature, pressure, and/or fuel quality sensors, may also be provided to the ECM and used to improve the accuracy of the virtual filter condition sensor. The ECM uses an algorithm to calculate the condition of the filter based on the time, torque, speed and other optional data. Adjustable parameters may be optionally entered into the ECM to refine the algorithm and adjust for differences between engines and filters, as well as local conditions, such as fuel quality and environmental conditions. These adjustable parameters can improve the accuracy of the calculation. Typically, the adjustable parameters are programmed into the ECM of new engines. Their values can be modified or adjusted once information is available regarding the intended use or final destination of the engine. The adjustable parameters can also be readjusted for existing engines to fine tune the sensor for local conditions. The result of the filter condition calculation is functionally transmitted to an output device, e.g., a visual indicator, colored light, fault or other informative code, digital indicator, appropriate data collection, and/or processing device such as a computer, ECM or controller (control circuit), whereby appropriate action can be taken based on this information.

The virtual filter condition sensor of FIG. 1 works as follows. Sensors, including those to measure engine speed 105 and whatever additional sensors 110 are required by the engine to calculate engine torque, as well as a means to monitor engine run time 115 are provided and transmit data to the ECM. Alternately, engine torque can be measured directly, such as by a surface acoustic wave (SAW) sensor on the cam shaft. The ECM calculates engine torque (130), as is typically done in modern diesel engines. An algorithm 145 resident in the ECM receives the engine torque data 130, engine speed data 125 and time data 135 periodically or on a near continuous basis and uses the various data to determine the impact of current conditions on filter life. The algorithm 145 can also rely upon various adjustable parameters 150 in determining the filter condition 155. The algorithm 145 can also consider the presence or absence of a filter (represented at 140), based upon an appropriate filter sensor 120. Cumulatively, the results over time during a filter service interval provide a continuous or periodically updated estimate of the current condition of the filter (155).

The ECM generates a signal corresponding to the condition of the filter that is sent to an output device 160, such as a display or other device, to prompt or initiate an appropriate response. In the embodiment represented by FIG. 1, the mechanism for calculating/determining the engine run time 115, the engine torque calculation 130, the time calculation 135, the algorithm 145 and the filter condition determination 155 are resident on the ECM.

On-board sensors, such as engine speed sensors, are present on modern diesel engines and can be used to control and optimize engine performance and function. From these, other important parameters, such as engine torque may be calculated. The virtual sensor receives engine torque, engine speed, and engine run time data. Thus, all sensors needed to calculate engine torque, as well as engine speed sensors can be utilized. The means for measuring or calculating torque is well known in the field, as modern diesel engines typically possess this capability. Additional sensors or means to determine fluid flow rates, pressure, temperature, fluid quality, and other parameters optionally may be used to improve the accuracy of the calculation and reliability of the virtual filter condition sensor. The on-board sensors provide inputs to the ECM to enable engine torque to be calculated and to determine filter condition. Measured values such as pressure and temperature are considered relative to the location of the respective sensor. For example rail pressure and injector return line temperature can be considered.

The on-board sensors discussed herein can be located at various locations on the engine. By way of example, fuel pressure may be measured at the accumulator (rail) on various diesel engines. The fuel pressure can be measured at other locations on the engine as well, including, but not limited to, the fuel inlet, the filter inlet, the filter outlet, the ECM cooler outlet, the low pressure pump inlet, the low pressure pump outlet, the high pressure fuel pump inlet, and the engine fuel return. In particular implementations, sensors may also be used to measure engine characteristics such as the temperature(s) at the fuel inlet, the ECM cooler outlet, the high pressure fuel pump inlet, the high pressure fuel pump outlet, the accumulator fuel return, the engine fuel return, and the injector return. It should be noted, however, that many of the above sensors may not be included in various implementations.

Sensors could also be used to measure various characteristics of the lube system. These sensors may measure, for example, the oil cooler inlet temperature, the oil cooler outlet temperature, the oil pan temperature, the oil cooler inlet pressure, the oil cooler outlet pressure, the oil filter inlet pressure, the oil filter outlet pressure, the block inlet pressure, the oil rifle temperature and the pump outlet pressure. It should be noted, however, that many of the above sensors may not be included in various implementations.

Since the accuracy of the filter condition calculation depends, in part, on the characteristics of the filter, the system optionally can include a sensor to determine whether or not an appropriate filter has been installed. Examples of such sensors are described in U.S. Pat. Nos. 6,533,926, 6,537,444, 6,711,524 and US 2011/0220560, which are incorporated herein by reference. With this option, the engine possesses a sensor capable of detecting a property, tag, or signature, such as a memory chip, surface acoustic wave chip, electrical resistance, magnetic, or other property that is uniquely present in appropriate filters. Further, the sensor can provide an output to the ECM identifying the filter as appropriate (or not). In some embodiments, the sensor is capable of not only determining whether or not the filter is genuine, but the type of filter installed. Depending on the whether or not an appropriate filter is installed, adjustable parameters can be selected by the algorithm that are appropriate to the circumstances.

Typically, modern engines have an electronic control module, ECM. The ECM is an on-board computer, and/or controller (control circuit) that accept inputs from engine sensors and utilizes algorithms and lookup tables to control engine processes and functions, calculate torque, report conditions and take otherwise appropriate actions. The ECM can comprise a control circuit having one or more control modules or sections, each having a memory and a processor for sending and receiving control signals and for communicating with peripheral devices, including additional control circuits, sensors, input devices and output devices. The ECM is connected to a computer readable medium that includes volatile or nonvolatile memory upon which computer readable code is stored. The processor accesses the computer readable code and the computer readable medium upon executing the code carries out the functions described herein. It is also to be understood that while the computer readable medium can be separate from the processor, the computer readable medium may be a part of the processor or integrally connected to the processor while in still further embodiments the computer readable medium may be implemented as a plurality of computer readable media for access by the processor. Different modes of operation can be programmed into the control circuit, as further described herein below. The programming and control operations of the control circuit are described herein with respect to non-limiting examples and algorithms. Some of the examples/algorithms include specific series of steps for accomplishing certain system control functions. However the configuration of the control circuit and any related control circuit modules and/or sections can substantially vary from that which is shown and described. The scope of this disclosure is not intended to be literally bound by the literal order and content of steps described herein and thus non-substantial differences and/or changes are intended to fall within the scope of the disclosure. In general, the control circuit includes a programmable processor and a memory for storing information. The control circuit can also be connected for sending and receiving signals with the noted peripheral devices via wired and/or wireless links.

According to this disclosure, the ECM can have a memory and programming that contains an algorithm and/or lookup table that provides the added function of determining the condition of fuel and/or lube filter(s). The algorithm may do this in a variety of ways. For example, it may use a filter life map (described later) to determine the incremental amount of the filter's life used up by the engine running at current conditions. By summing the incremental amounts over the period of time during which the filter has been installed, and comparing the sum to the expected life of the filter under known conditions, the condition of the filter and its remaining useful life can be estimated. In another embodiment, the time-weighted average duty cycle of the engine, based on torque and speed data over the corresponding time interval can be compared to a filter life map to estimate the condition of the filter and/or compared to the expected filter service interval to determine its remaining useful life. If an optional appropriate filter detection sensor is used, the algorithm may elect to use one set of adjustable parameters for appropriate filters, and a different set (or not to provide filter condition information at all) if an inappropriate filter is used.

Figure 3:
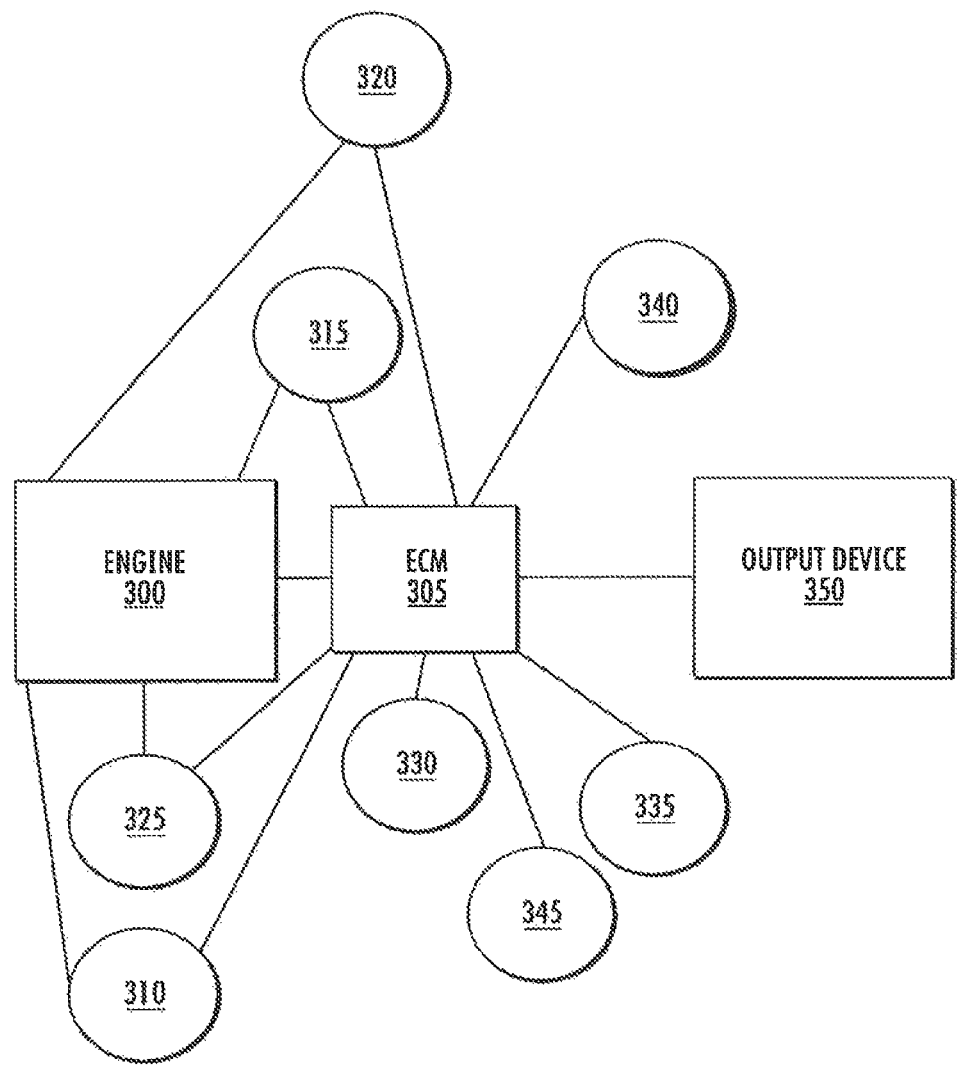
FIG. 3 is schematic representation of a system for implementing various embodiments described herein.

FIG. 3 is schematic representation of a system for implementing various embodiments described herein. As shown in FIG. 3, an engine 300 is communicatively connected to an engine control module 305 or a similar control unit. The engine control module 305 is also communicatively connected to a plurality of sensors, each of which is used to provide data to the electronic control module 305 for manipulation and inclusion in an algorithm to determine the condition of the filter. The plurality of sensors may include, but are not limited to, an engine speed sensor 310, an air intake manifold pressure sensor 315, a throttle position sensor 320, an engine pressure sensor 325, a fuel quality sensor 330, a filter detection sensor 335, a filter condition sensor 340 and an "appropriate filter" sensor 345. Some or all of these sensors may also be directly or indirectly connected to the engine 300. The engine control module 305 is also electrically and/or communicatively connected to an output device 350, through which determined filter condition information is output.

The inventors have observed that filter life for engine lube oil and for fuel filters is a function of engine operating conditions. The inventors have found that filter life is shortened by severe or heavy duty usage, for both lube and fuel filters. In contrast to lube oil, fuel is burned. Thus, one would expect fuel filter life to be controlled by contaminants in the supply fuel, and to a lesser extent by engine operating conditions. Despite this, data surprisingly has shown that fuel filter life is shortened by severe or heavy duty usage. Lube oil, on the other hand is recirculated indefinitely until it is replaced. Remaining engine oil life, but not oil filter life, has been determined from a knowledge of temperature, fueling rate, engine speed and load (see GB2345342B), which is incorporated herein by reference. U.S. Pat. No. 6,253,601 which is incorporated herein by reference, describes a system and method to determine when the oil should be replaced based on engine parameters such as engine temperature, fueling rate, engine speed, and engine load. Other methods exist for estimating the condition of the oil, but not for determining the condition of the oil (or fuel) filter. The condition of the oil filter is a function of the solid and semi-solid contaminant removed. Thus, while the filter's condition may be related to the condition of the oil, other factors affect filter life as well.

Figure 2:
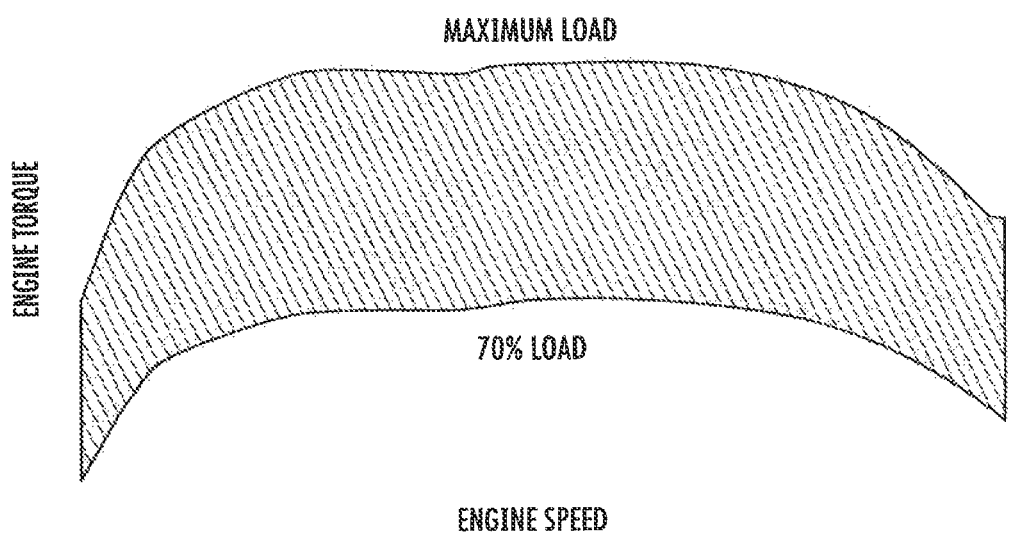
FIG. 2 is an exemplary engine torque versus speed plot, showing the engine torque versus engine speed at both maximum load and at 70% maximum load.

Duty cycle is a term used to describe the severity of engine operating conditions and can be defined in various ways using input from engine sensors. One way is to define duty cycle as the power generated to overcome load using an engine torque versus speed plot, as shown in FIG. 2. In the figure, the shaded region is bounded by lines representing the maximum load and 70% of maximum load as a function of speed. This region may be defined as the severe or heavy duty cycle for the engine. The relationship between engine torque and speed, and filter life can be mapped by means of engine tests under controlled conditions using an engine dynamometer. Using the filter life map, the effect of specific torque and speed conditions on filter life can be determined relative to reference conditions that correspond to the normal filter service interval for the engine. Correspondingly, this information can be used on a continuous or periodic basis to estimate the condition of the filter.

There are other means of creating a filter life map or quantitatively modeling engine operating conditions and relating them to filter life. For example, duty cycle can be defined as the ratio of the time-weighted average produced power to the engine rated power; the percentage of time that the engine operates at rated power (or some fraction of rated power); percentage of time, miles, or fuel consumed at different RPM, torque or rail pressures; or some combination of two or more of the previously listed definitions. Any of these can be used to define a filter life map or in an algorithm to relate engine operating conditions to filter life.

The present disclosure can also utilize optional adjustable parameters to improve the accuracy of the calculation. The values for the adjustable parameters are typically held constant during a service interval and depend on the type of engine and filter, local fuel or lube oil quality, and local and environmental factors. Typically, one (1) to six (6) adjustable parameters are needed; however more may be needed for more complex algorithms and models. For example, adjustable parameters may be needed to account for the characteristics of the engine, filter, and liquid. Typically, default values for the adjustable parameters will be programmed into the ECM for use by the algorithm based on the anticipated normal conditions for the engine and application. These values can be changed as necessary manually, electronically, or otherwise before or after the engine is used, if conditions are expected to differ from the default settings. For example, different values for the adjustable parameters may be used for engines used in urban bus applications in North America, as opposed to those making deliveries in Asia. If an optional appropriate filter sensor is used, one set of values can be used when installation of an appropriate filter is confirmed. Another set of values may be used when an inappropriate filter is installed, in order to provide a more conservative estimate of filter condition and protect the engine. Alternatively, the algorithm may not calculate and indicate filter condition at all, if an inappropriate filter is used. The values for these parameters can also be readjusted later, such as by service personnel, based on experience and history at the location to improve the accuracy of the calculation. Typically, the adjustable parameters are input manually, but one or more may be provided automatically when appropriate sensors are present, electronically, or by other means.

An algorithm resident in the ECM can be used to calculate the condition of the filter. There are various forms of the algorithms that can perform the calculation, which differ in terms of data requirements, adjustable parameters, and accuracy of the results. All require torque, engine speed and time data. The following equation is one example of these:

$$R = E - \sum_{0}^{t}(ABX + CY)\Delta t$$

where R is the remaining useful life of the filter; E is the normal service interval of the filter; t is engine run time that the filter has actually been used; A, B and C are adjustable parameters; and X and Y are variables whose values are determined from torque and speed data. The values of A and C depend on the type of engine and filter. The value of B depends on the anticipated fuel quality. The values of X and Y are obtained from engine torque and speed data at a given point in time based on the filter life map or mathematical modeling of the relationship between the input data and these variables.

The virtual filter condition sensor, as described, can be used for either the fuel filter or the lube oil filter. In a further embodiment, the system may indicate the condition and/or remaining useful life of both the fuel and the lube oil filters. In the latter embodiment, no additional sensors would be required. Instead, a second algorithm and means of outputting the results would only be required.

In another embodiment, the virtual filter condition sensor can also include an electronic means of detecting the presence and installation of appropriate filters on the engine, in order to ensure the accuracy of the calculation. Values for one or more of the adjustable parameters are affected by the type of filter installed. If an electronic means of detecting appropriate filters is available to supply data to the algorithm, the algorithm could confirm that the proper filter is being used prior to providing filter condition outputs. If an inappropriate filter is installed, filter condition would be calculated or, alternatively, adjustable parameters would be used that conservatively calculate the condition of the filter, thus motivating the use of appropriate filters.

A virtual filter condition sensor is for determining the condition of fuel and/or lube oil filters based on engine torque, speed and run time data, and that does not require direct measurement of filter restriction (or pressure drop) nor flow rate through the filter. The virtual sensor could be used in conjunction with a means for determining pressure drop to further improve its reliability, however, this would be used as essentially independent or secondary measure of filter condition. The virtual sensor uses data from typical engine sensors or values that are calculated from these sensors by the ECM. The presently described systems can provide for the input of values for adjustable parameters related to the characteristics of the engine, filter, and liquid being filtered, and optionally regarding application and local conditions, to improve the accuracy of the results. Existing filter condition sensors, also known as filter life, filter plugging, or filter service indicators determine filter conditions typically based on pressure drop data, or possibly based on the volume of fluid filtered. Oil quality sensors are known to exist that predict lube oil quality using on-board sensors, but not the condition of the filter. Since fuel is burned rather than being completely recirculated, it is counterintuitive that engine conditions related to duty cycle would affect filter life, but this has indeed been confirmed by test cell and field test monitoring. Further, the same input parameters are utilized by both lube and fuel filter condition sensors, hence minimal additional requirements and no additional real sensors are needed to provide an engine with both types of virtual sensors. Finally, the presently described systems optionally can utilize an "appropriate filter" sensor to ensure that appropriate adjustable parameters are used by the algorithm.

Figure 4:
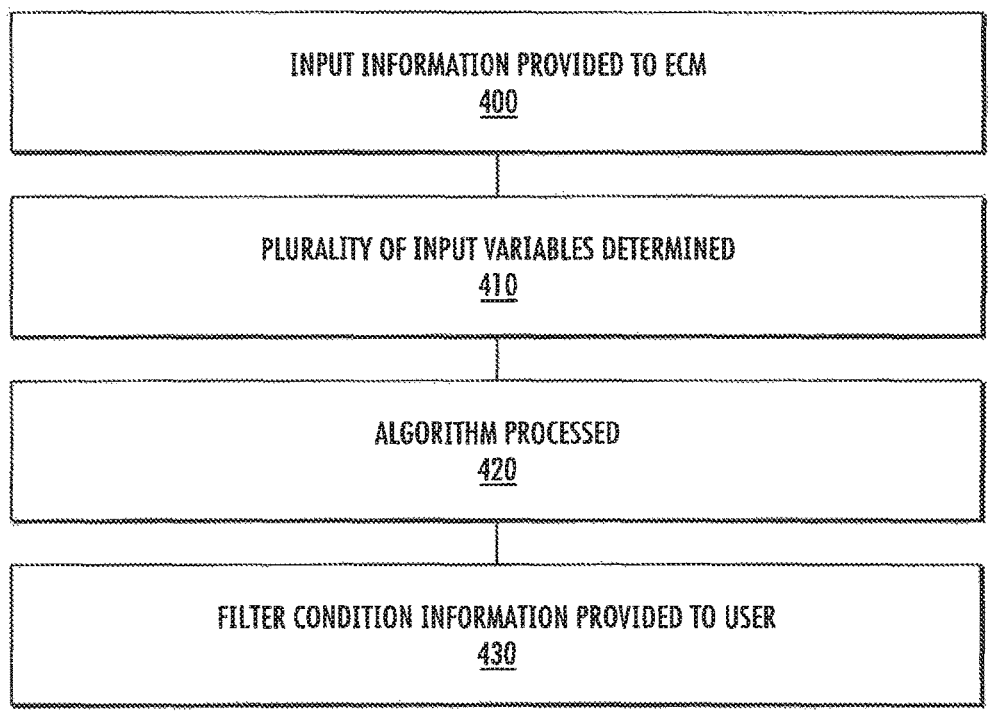
FIG. 4 is a flow chart showing an exemplary process by which various embodiments contained herein may be implemented.

FIG. 4 is a flow chart showing an exemplary process by which various embodiments contained herein may be implemented. At 400 in FIG. 4, input information from a plurality of sensors relating to the operation of the engine is provided to a control unit such as an ECM. At 410, at least a portion of input information is used to determine a plurality of input variables, the plurality of input variables representing a plurality of engine operating conditions. As discussed previously, the engine operating conditions which may be represented include, but are not limited to, engine run time, engine torque and engine speed. By way of example, an input variable representing engine torque may be based upon input information relating to at least one of air intake manifold pressure, throttle position and engine speed. At 420, an algorithm that incorporates the plurality of input variables is processed, resulting in a determination of a condition of the filter. As discussed previously, the algorithm may also directly or indirectly take into account direct input information, as well as other information including, but not limited to, duty cycle, whether an appropriate filter has been installed, engine operating environment, engine characteristics, filter characteristics, operator experience, engine temperature, engine temperature and fuel quality. At 430, information concerning the condition of the filter is output to a user such as a vehicle operator or service technician.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

It should be noted that any use of the term "exemplary" herein to describe various embodiments is intended to indicate that such embodiments are possible examples, representations, and/or illustrations of possible embodiments (and such term is not intended to connote that such embodiments are necessarily extraordinary or superlative examples).

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for determining a condition of a filter filtering fluid associated with an engine system, the system comprising:
    a plurality of sensors operatively connected to the engine system, the plurality of sensors configured to collectively provide information relating to engine run time, engine torque, and engine speed;
    an engine control module communicatively connected to the plurality of sensors, the engine control module configured to:
        receive the information from the plurality of sensors relating to engine run time, engine torque, and engine speed,
        using at least some of the received information to determine a plurality of input variables, the plurality of input variables representing a plurality of engine operating conditions including engine run time, engine torque, and engine speed;
        determine the condition of the filter based on an algorithm that incorporates the plurality of input variables; and
        outputting information relating to the condition of the filter.

2. The system of claim 1 wherein the plurality of sensors comprises a surface acoustic wave sensor on a cam shaft of the engine system, the surface acoustic wave sensor directly measuring engine torque.

3. The system of claim 1 wherein the plurality of sensors comprises an engine speed sensor, and wherein the engine control module uses information from the at least one engine speed sensor to calculate engine torque.

4. The system of claim 1 wherein the engine control module is configured to calculate the engine torque based on at least one input selected from the group consisting of air intake manifold pressure, throttle position and the engine speed.

5. The system of claim 1 further comprising a sensor configured to sense engine temperature, engine pressure, and fuel quality, wherein the algorithm further incorporates the engine temperature, engine pressure and fuel quality.

6. The system of claim 1 further comprising a. sensor operatively connected to the engine system and configured to sense engine pressure, wherein the algorithm further incorporates the engine pressure.

7. The system of claim 1 further comprising a sensor operatively connected to the engine system and configured to sense fuel quality, wherein the algorithm further incorporates the fuel quality.

8. The system of claim 1 wherein the algorithm further incorporates a variable that varies based upon an engine operating environment.

9. The system of claim 1 wherein the algorithm further incorporates a variable that varies based upon an engine characteristic.

10. The system of claim 1 wherein the algorithm further incorporates a variable that varies based upon, a lube oil filter characteristic.

11. The system of claim 1 further comprising a sensor configured to detect whether an appropriate lube oil filter has been installed in the engine; and wherein the algorithm further incorporates whether the appropriate lube oil filter has been installed in the engine.

12. The system of claim 1 further comprising an output device configured to notify an operator of the condition of the filter; wherein the engine control module is configured to operate the output device.

13. The system of claim 1 wherein the condition of the filter comprises remaining useful life of the filter.

14. The system of claim 1 wherein the algorithm is represented by the formula $$R = E - \sum_{0}^{t} (ABX + CY)\Delta t$$

wherein R is a remaining useful life of the filter; E is a normal service interval of the filter; t is an input variable representing engine run time that the filter has actually been used; X is an input variable representing engine torque, and Y is an input variable representing engine speed.

15. The system of claim 14, wherein the value of A is dependent upon a type of engine used, wherein the value of B is dependent upon anticipated fuel quality, and wherein the value of C is dependent upon a type of filter used.

16. The system of claim 1 wherein the algorithm further incorporates duty cycle.

17. A system for determining a condition of a filter filtering fluid
associated with an engine system, the system comprising:
a plurality of sensors operatively connected to the engine system, the plurality of sensors configured to collectively provide information relating to engine run time, engine torque, and engine speed;
an engine control module communicatively connected to the plurality of sensors, the engine control module configured to:
receive the information from the plurality of sensors relating to engine run time, engine torque, and engine speed,
using at least some of the received information to determine a plurality of input variables, the plurality of input variables representing a plurality of engine operating conditions including engine run time, engine torque, and engine speed;
determine the condition of the filter based on a lookup table that takes into account the plurality of input variables; and
outputting information relating to the condition of the filter.

18. The system of claim 17, wherein the plurality of sensors comprises a surface acoustic wave sensor on a cam shaft of the engine system, the surface acoustic wave sensor directly measuring engine torque.

19. The system of claim 17, wherein the plurality of sensors comprises an engine speed sensor, and wherein the engine control module uses information from the at least one engine speed sensor to calculate engine torque.

20. The system of claim 17, wherein the engine control module is configured to calculate the engine torque based on at least one input selected from the group consisting of air intake manifold pressure, throttle position and the engine speed.

* * * * *